United States Patent [19]
Chase

[11] Patent Number: 5,343,875
[45] Date of Patent: Sep. 6, 1994

[54] PROTECTIVE DEVICE

[75] Inventor: Marjorie L. Chase, Delta, Canada

[73] Assignee: Superior Diapering Products Ltd., Delta, Canada

[21] Appl. No.: 952,397

[22] Filed: Sep. 28, 1992

[51] Int. Cl.⁵ .................. A61G 15/00; A61M 5/00; A61F 5/37

[52] U.S. Cl. .................. 128/846; 604/263; 128/DIG. 26; 128/877

[58] Field of Search ............ 128/845, 846, DIG. 26, 128/877; 604/110, 162, 163, 177, 263; 206/364, 365, 571

[56] References Cited

U.S. PATENT DOCUMENTS

| | | | |
|---|---|---|---|
| 3,059,645 | 10/1962 | Hasbrouck | 128/DIG. 26 |
| 3,574,306 | 4/1971 | Alden | 604/162 |
| 3,696,920 | 10/1972 | Lahay | 128/DIG. 26 |
| 4,282,871 | 8/1981 | Chodorow | 128/DIG. 26 |
| 4,559,042 | 12/1985 | Votel | 604/192 |
| 4,585,444 | 4/1986 | Harris | 604/177 |
| 4,606,735 | 8/1986 | Wilder | 128/DIG. 26 |
| 4,820,282 | 4/1989 | Hogan | 128/DIG. 26 |
| 4,846,807 | 7/1989 | Safadago | 604/179 |
| 4,883,469 | 11/1989 | Glazier | 604/192 |
| 4,935,011 | 6/1990 | Hogan | 604/177 |
| 4,969,876 | 11/1990 | Patterson | 604/171 |
| 5,002,561 | 3/1991 | Fisher | 606/210 |

FOREIGN PATENT DOCUMENTS

| | | |
|---|---|---|
| 2036367 | 8/1991 | Canada . |
| 2056927 | 6/1992 | Canada . |

*Primary Examiner*—Michael A. Brown
*Attorney, Agent, or Firm*—Cooley, Godward, Castro, Huddleson & Tatum

[57] ABSTRACT

A protective device to protect against needle stick injuries in health care. The device has a base. There are troughs in the base to receive and protect fingers. Each trough has an inner wall that, with the other inner side wall defines a retaining passage between the troughs and on its inner surface a grip for the fingers. The device may also be able to hold a sample tube and include an indent adjacent one edge to place over a subcutaneous implanted injection port.

7 Claims, 2 Drawing Sheets

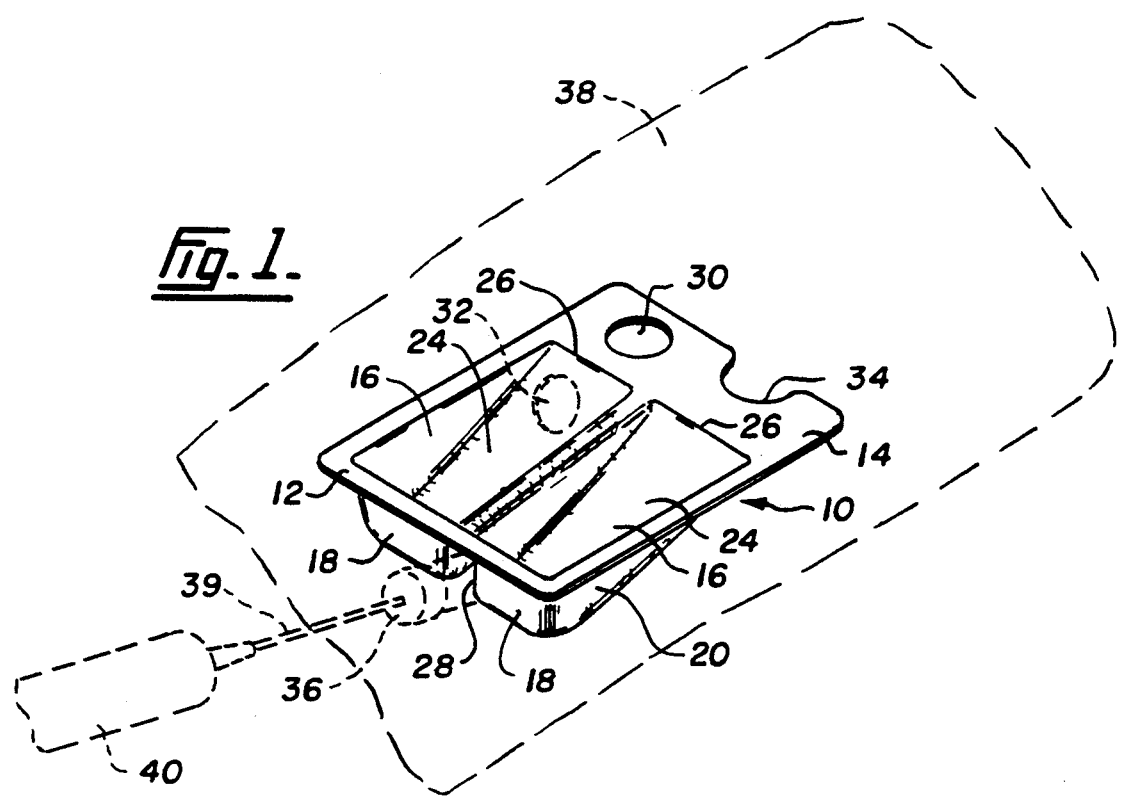
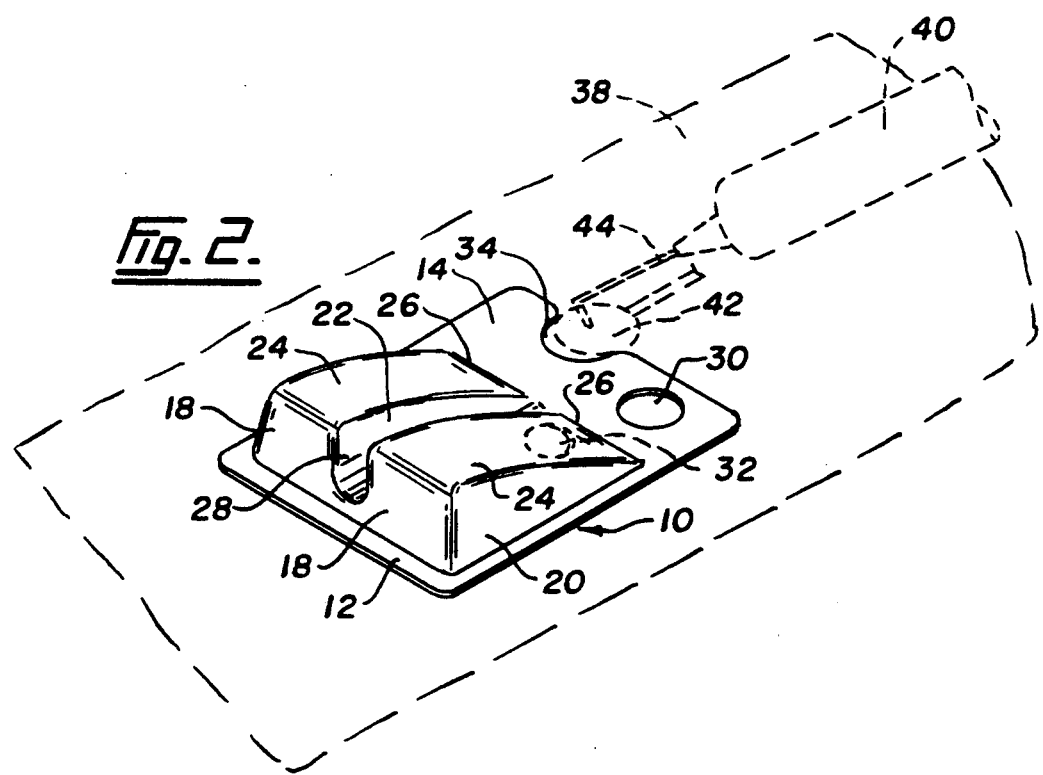

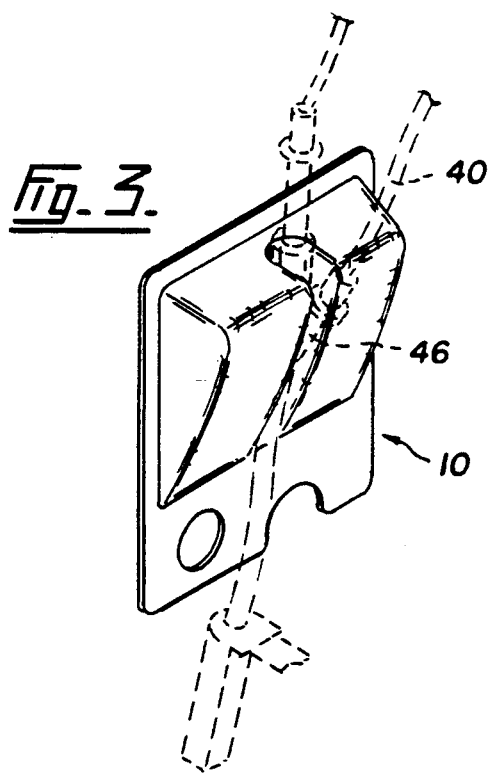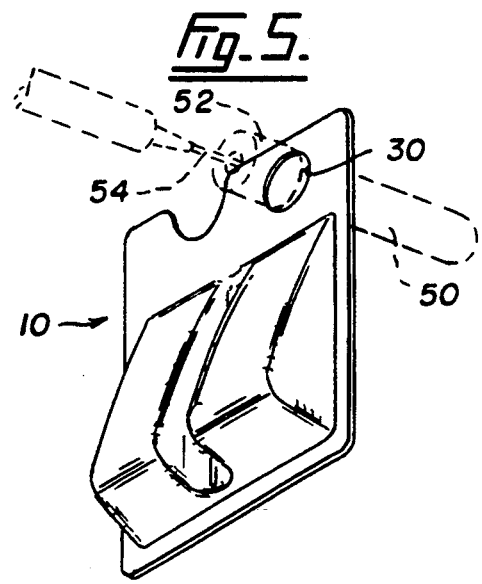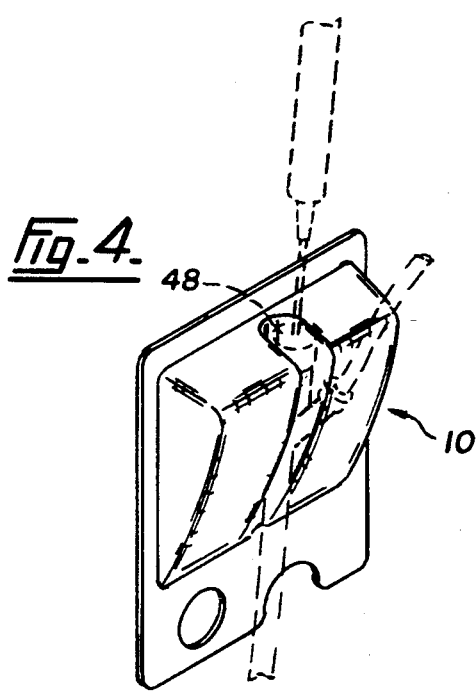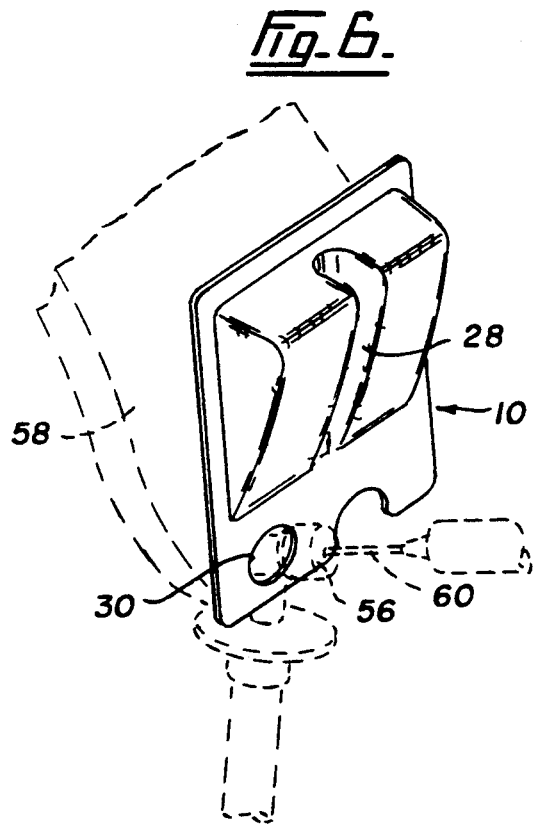

PROTECTIVE DEVICE

FIELD OF THE INVENTION

This invention relates to a protective device useful to protect against needle stick injuries in health care.

DESCRIPTION OF THE PRIOR ART

Injuries to health care workers by the use of "sharps" are common. A sharp may be defined as anything used in health care that has a sharp edge or point.

Needle stick injuries are injuries resulting from punctures by hypodermic needles, catheters and the like. Injuries from sharps have always been a hazard in health care work. In addition to the cuts and pricks that result there has, of course, always been the risk of infection. However, these seemingly minor injuries can now be life-threatening, particularly due to the occurrence of the HIV virus, hepatitis and other contagious diseases. There have been reported cases where health care workers have contracted AIDS through coming into contact with needles that have been used to inject patients having AIDS.

There have been several suggestions to provide protection against needle stick injuries.

For example, Hogan in U.S. Pat. No. 4,935,011 describes a sheath for an intravenous (IV) needle having foldable panels and being slidably mounted on a tube, connected to a needle for movement so that it can cover the needle while the needle is inserted and during and after retraction of the needle.

Safadago in U.S. Pat. No. 4,846,807 describes a mechanism securing an IV tube extending from an IV needle inserted in a patient. The mechanism includes an anchor that can be secured to the patient adjacent the puncture area of the IV needle. The anchor has a generally U-shaped cut defining an opening and the tube can be secured by a flat normally closing the opening but raisable relative to the remainder of the anchor member to receive the IV tube.

Hogan in U.S. Pat. No. 4,820,282 teaches a protective disposable sheath for hypodermic needles having butterfly shaped side strips. The sheath has a continuous flat base plate and two upper walls approximately horizontal to and terminating in spaced apart edges near the base plate mid-section. The upper walls are positioned above the base plate, at least near the mid-section, to provide a recess for receipt of needle side strips. The needle side strips can be retained so that they can enter but cannot be withdrawn from the recess.

Patterson in U.S. Pat. No. 4,969,876 describes a needle protector having a curved portion to capture the needle in an outer tube. The outer tube has a length so that when the trailing portion is pulled rearwardly, the needle moves rearwardly in the outer tube to be totally contained in the outer tube. The sharpened end is positioned inwardly from a constriction and is thus protected.

Fisher in U.S. Pat. No. 5,002,561 teaches protective hand forceps of a generally U-shape. There is a thumb casing portion and an index finger portion. There is a flexible hinge region and a continuous skirt.

SUMMARY OF THE INVENTION

The present invention seeks to provide a protective device that is simple in structure, can be made economically and easily and offers excellent protection against needle pricks.

Accordingly, and in its broadest aspect, the present invention is a protective device to protect against needle stick injuries in health care comprising a base; troughs in the base to receive and protect fingers; each trough having an inner side wall that, with the other inner side wall, defines a retaining passage between the troughs and a grip for the fingers on the sides remote from the retaining passage.

DESCRIPTION OF THE DRAWINGS

The invention is illustrated in the drawings in which:

FIG. 1 is an isometric view of a protective device according to the present invention in position on a patient;

FIG. 2 is a view similar to FIG. 1 illustrating a further use of the invention;

FIGS. 3 to 6 illustrate further uses of the protector device of the present invention.

DESCRIPTION OF THE PREFERRED EMBODIMENTS

The drawings show a protective device comprising a base 10. The base comprises a peripheral apron 12 having a relatively wide area 14 at one end. There are troughs 16 formed in the base 10, each trough 16 is shaped to receive one finger of a health care worker. The troughs 16 are of generally triangular section and deepen towards wall 18 at one end to protect the fingers. The troughs have outer side walls 20, inner side walls 22, the base 24 curving upwardly from the end wall 18 to join the area 14 at 26. The inner walls 22 define between them a passage 28.

There is a circular opening 30 formed in the wide area 14 of the base 10. Both FIGS. 1 and 2 show an opening 32 in broken lines which is an alternative position for the opening 30.

There is also a semi-circular indent 34 formed in the relatively wide area 14.

The passage 28 is able to grip a tubular body pressed between the inner side walls 22. If necessary the inner side walls 22 can be formed with roughened portions, for example ridges, to improve the grip of the side walls 22 on the tubular body. The passage 28 may also narrow towards the base 10, again to improve grip.

Various uses of the device of the present invention are shown in the drawings.

Referring first to FIG. 1, there is shown an intermittent injection cap 36 threadedly attached to an IV catheter, which is a component well known in the art and only the wider portion of which is shown. The remaining portion is inserted into the arm 38 of a patient in entirely conventional manner. The cap allows an IV tube to be connected when required by inserting a needle, connected to the IV tube, through the cap 36.

In the use illustrated in FIG. 1 the following procedure applies:

First the injection cap 36 is cleansed, typically with alcohol. The device of the invention is placed over the injector cap 36 with the passage 28 engaging the injector cap 36 as shown in FIG. 1. The device is gripped firmly with the fingers, typically of the non-dominant hand, that is the left hand of a right handed person and the right hand of a left handed person. The thumb is on one side, the remaining fingers on the other side of the inside of the passage 28, the position shown upwardly in FIG. 1. The dominant hand then brings up a needle 38 on the IV tube 40 to insert the needle into the cap 36. Injection may then take place in conventional manner. If necessary the device may be left in position on the intermittent injection cap 36.

FIG. 2 illustrates the use of the semi-circular indent 34. In this use indent 34 is placed over a subcutaneous implanted injection port 42. Such ports are frequently used in the treatment of AIDS patients. Relative to the FIG. 1 position the device is inverted and the fingers of the non-dominant hand grip the outer walls 20 of the troughs. The injection port is located by palpation and, with the fingers protected on the walls 20, and thus remote from a needle 44, the needle may be inserted into the port. The device is useful in both entry of the needle and removal of the needle. With these subcutaneous ports 42, the needle is L-shaped, as shown in FIG. 2.

FIG. 3 shows the protective device in place on a Y-injection site 46. The procedure involves holding the Y-injection site 46 opposite to the injection port, cleansing the injection port as appropriate, for example with alcohol, and sliding the Y-injection site 46 down into the passage of the device according to the invention with the non-dominant hand. The needle may be inserted into the injection port, with the fingers protected in the troughs 16.

FIG. 3 shows the use of the device with a continuous IV system. FIG. 4 shows the use of an intravenous injection port 48, in a manner similar to FIG. 1.

The device may stay attached to the upper Y-injection site to provide continuous needle protection and continuous safe access to the system or to the lower injection site to provide continuous safe injection of medication into the port.

FIG. 5 illustrates the use of opening 30. The opening holds a sample tube 50. The opening 30 is dimensioned to receive the tube 50 which has a cap 52. The tube, with the cap in place, is placed through the opening 30. The sample tube is grasped with the non-dominant hand, behind the protector. A syringe needle 54 is inserted into the sample tube 50 and the tube is filled.

FIG. 6 shows a further use of the opening 30. An injection cap 56 of an intravenous bag 58 is positioned through the opening 30. The protective device is held against the bag 58 and a syringe needle 60 is inserted into the cap 56. Appropriate medication may then be inserted into the bag 58. The syringe is removed. In this application the fingers are protected and so is the bag 58.

The device of the present invention can also be used to cap a needle after use. To this end the cap, which is a simple cylinder longer than the needle, may be inserted into the passage 28. The needle is inserted into the protective cover while the device is gripped with the fingers inside the troughs. The capped needle is removed from the protector by pushing the capped needle forward through the passage 28.

The present invention thus provides a protective device that is useful in a wide range of circumstances in health care.

The protective device may be moulded with great ease from plastic. Polystyrene has been used. Injection moulding, vacuum moulding and the like well known moulding techniques are suitable.

I claim:

1. A protective device to protect against needle stick injuries in health care comprising:
   a base;
   a pair of troughs in the base to receive and protect the fingers, where the bottom of said pair of troughs is located in a plane different from that of the base, and
   each trough has an inner side wall and an opposed outer side wall; where the opposing inner side walls of the troughs are connected at the top of the trough, defining a retaining passage between the troughs and a grip for the fingers on the surface remote from the retaining passage.

2. A protective device as claimed in claim 1 in which the base comprises a peripheral apron having a relatively wide area at one end.

3. A protective device as claimed in claim 2 including means to hold a sample tube.

4. A protective device as claimed in claim 3 in which the means to hold a sample tube comprises an opening dimensioned to receive the sample tube.

5. A protective device as claimed in claim 1 including an indent adjacent one edge of the relatively wide area to place over a subcutaneous, implanted injection port.

6. A protective device to protect against needle stick injuries in health care comprising:
   a base comprised of a peripheral apron having a relatively wide area at one end with an opening dimensioned to receive a sample tube;
   a pair of troughs in the base to receive and protect fingers;
   each trough having an inner side wall and an opposed outer wall, said inner side walls of said trough defining a retaining passage between said troughs and a grip for the fingers on the sides remote from the retaining passage, the troughs depending towards a wall at one end to protect the fingers.

7. A protective device as claimed in claim 6 in which an opening dimensioned to receive said sample tube is in at least one of said troughs.

* * * * *